United States Patent [19]

Barnett

[11] Patent Number: 5,460,798
[45] Date of Patent: Oct. 24, 1995

[54] SYSTEM FOR DETERMINING THE QUANTITY AND IDENTITY OF MATERIAL INGESTED BY USER

[76] Inventor: Patrick A. Barnett, 1046 Highland Rd., Brentwood, Tenn. 37027

[21] Appl. No.: 100,027

[22] Filed: Jul. 26, 1993

Related U.S. Application Data

[63] Continuation-in-part of Ser. No. 902,576, Jun. 22, 1992, abandoned.

[51] Int. Cl.⁶ .................................................. A61K 49/04
[52] U.S. Cl. ................................................................ 424/9.4
[58] Field of Search ........................... 424/2, 4, 5, 9, 424/6

[56] References Cited

U.S. PATENT DOCUMENTS 3,341,417  9/1967  Sinaiko ........................... 167/84.5
4,367,216  1/1983  Mutzel et al. ........................ 424/5

FOREIGN PATENT DOCUMENTS 0708096  4/1954  United Kingdom .

Primary Examiner—Glennon H. Hollrah
Assistant Examiner—Brian M. Burn
Attorney, Agent, or Firm—Waddey & Patterson; I. C. Waddey, Jr.

[57] ABSTRACT

The present invention provides a device and method for determining the quantity and identity of a substance ingested by a user. A detectable material such as barium sulfate is formed into a marker and mixed with a foreign substance such as pills, capsules, caplets, poisons or other hazardous substances. This detectable marker resides in the individual's digestive tract until passed. This material is detectable by use of X-ray equipment or a fluoroscope allowing the attending physician to "see" into the individual's digestive tract to determine the quantity of foreign substance ingested by counting the number of markers. Further, if the detectable markers have a unique geometric shape, the physician can identify the ingested substance associated with that shape of marker.

9 Claims, 2 Drawing Sheets

SYSTEM FOR DETERMINING THE QUANTITY AND IDENTITY OF MATERIAL INGESTED BY USER

This is a continuation-in-part of U.S. patent application Ser. No. 07/902,576, filed Jun. 22, 1992 now abandoned.

BACKGROUND OF THE INVENTION

The present invention relates generally to a device which allows determination of the number and identity of objects in a user's stomach and more particularly to a detectable pellet or marker which is mixed with objects such as capsules, caplets, pills, poisons or other hazardous substances which can be detected by use of a fluoroscope, on X-ray film, or by other X-ray techniques while resident in a user's digestive tract.

It will be appreciated by those skilled in the art that when someone has overdosed on drugs, or ingested poisons or other hazardous substances, the attending physician often needs to know the extent and identity of the overdose to determine what treatment, if any, to give the patient or the dosage of antidote to prescribe. It will be further appreciated by those skilled in the art that oftentimes such victims are not able to communicate to the attending physician the number of pills, capsules, or caplets taken or the amount of poison or hazardous substance ingested. This inability to communicate is particularly true in the pediatric and geriatric patients as well as the unconscious; patient. Because of the condition of such victims, the attending physician must be able to determine the quantity of pills taken, or the amount of poison or hazardous substance ingested, without any intrusive procedure such as surgery or endoscopy, which have high attendant risks. It appears, however, that there have been relatively few attempts to develop a system to determine the quantity of pills, or the amount of poison or hazardous substance ingest by an individual.

U.S. Pat. No. 4,274,550 issued to G. Feldstein on Jun. 23, 1981, discloses a medicant dispensing device. Although this device may discourage the user from taking an overdose of a medicant, the system can not determine how many pills have actually been taken if the pills have been taken from different containers.

U.S. Pat. No. 3,341,417 issued to E. Sinaiko on Sep. 12, 1967, discloses a radiopaque marker which is incorporated into a dosage unit of a drug marketed for oral ingestion. However, the marker must be molded in with the drug material during the actual manufacture of the pill itself.

Each of the prior art approaches requires the maker of the medicant to integrate the radiopaque marker in with the pills during the original manufacturing process. In particular, there is no provision for the; purchaser, or user, of the medication to retroactively mark the pills with a radiopaque substance. Further, there is no discussion in the prior art of a device for marking poisons and other hazardous substances which are not intended to be intentionally ingested in the first place.

What is needed, then, is a device to determine the quantity and identity of materials ingested by a user and which can be retroactively combined with the ingestible material after such ingestible material has been purchased, or otherwise obtained, by the user. This device must be capable of determining the contents of an individual's digestive tract without intrusive procedures. This device must be capable of use with any material such as a caplet, capsule, or pill or with poisons or other hazardous substances. This device is presently lacking in the prior art.

In this application, it will be appreciated by those skilled in the art that while I describe my invention in terms of detecting pills, capsules, caplets, poisons or other hazardous substances in the digestive tract of a person, my invention is designed to aid in the detection of pills, etc. in animals (particularly dogs, cats, horses and cattle) as well as in humans. Also, the substance can be detected at various locations in the body including the stomach, the esophagus, the intestinal tract or in passage. Lastly, the item to be detected can be any kind of pill, capsule, caplet or their equivalent, or a liquid or powder substance as hereinafter provided.

SUMMARY OF THE INVENTION

The present invention overcomes deficiency of the prior art by providing a device to assist in determining the quantity of a foreign material in the body of a living creature. More specifically the present invention assists in determining the number and identity of substances ingested by a user. Any X-ray detectable material such as barium sulfate is mixed with the objects such as pills, capsules, caplets, poisons or other hazardous substances. This detectable material resides in the individual's digestive tract until passed. This material is detectable by use of a fluoroscope or X-ray film allowing the attending physician to "see" into the individual's digestive tract in order to determine the quantity of material ingested by counting the number of pellets or markers.

According, one object of the present invention is to provide a device for determining the quantity of foreign material in the body of a living creature.

Another object of the present invention is to provide a device, method and system for determining the units or quantity of foreign substance in the body of a human or an animal.

Still another object of the present invention is to provide such a device, method and system which is not intrusive.

Still another object of the present invention is to provide a device, method and system which can be integrated with any capsule, caplet, or pill or with liquid or powder.

Still another object of the present invention is to provide a method for labeling, via one or more radiopaque markers, the identity of medications, poisons and other hazardous substances.

DESCRIPTION OF THE PREFERRED EMBODIMENT

Figure 1:
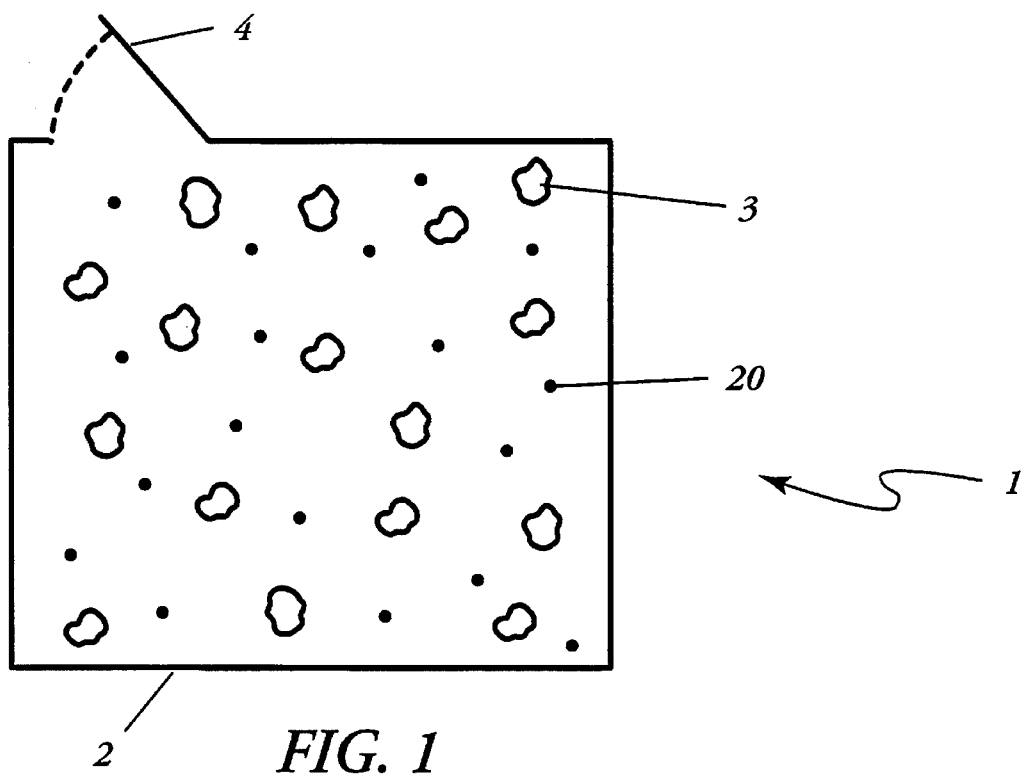
FIG. 1 is a side view of several radiopaque markers mixed in with a poisonous substance contained in a box.

Referring now to FIG. 1 there is shown generally at 1 an embodiment of the present invention. Housing 2 may be a box, carton or similar enclosure which contains poisonous pellets 3 or another hazardous substance. After purchasing the poison, the customer opens lid 4 and dumps a quantity of radiopaque markers 20 into the box. The box is then shaken to, more or less, homogeneously mix the markers with the poisonous pellets. Then, in the event that a child, or other individual, ingests poison from the box he will, in all likelihood, also ingest one or more of the radiopaque markers at the same time. Thus, by use of a fluoroscope or by taking an X-ray, the attending physician can "see" the radiopaque markers and thereby confirm that the child has ingested material from the box of poison. Further, the number of markers that the physician sees gives a rough approximation of the amount of poison that was ingested.

Figure 2:
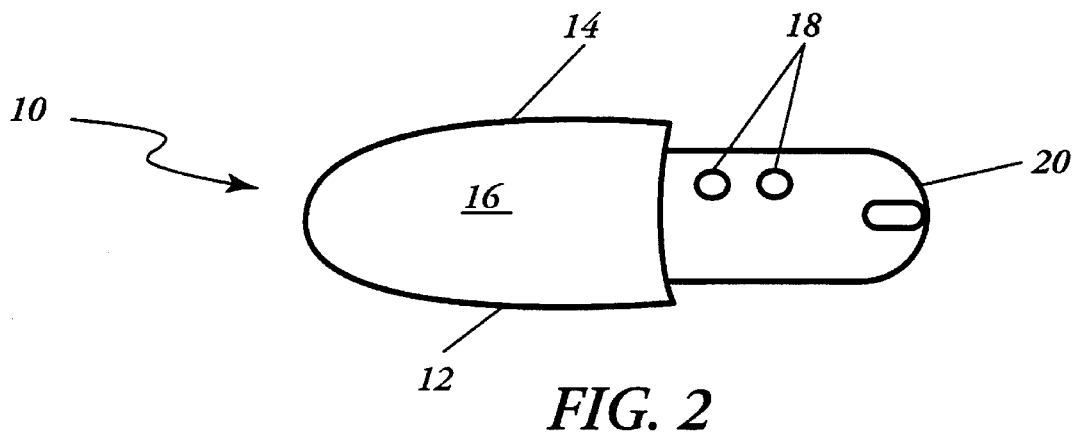
FIG. 2 is a side view of the device for determining the number of objects taken by a user in the preferred embodiment as it is adhesively attached to the housing of a capsule.

Referring now to FIG. 2 there is shown generally at 10 another embodiment of the device for determining the number of objects taken by a user. In this instance, object 12 is capsule 14. However, detectable pellet 20 is adhesively attached to the outside of housing 16. Housing 16 encloses time release pellets 18, or other non-time release medication. Detectable pellet 20 can be affixed to housing 16 using any well known adhesive which is digestible. Any other workable marker, including a time release pellet, other pellet or structure impregnated with X-ray absorbing material, may be used. The capsule itself, or the outer surface of a tablet, may be coated by dipping, spraying, dusting or other means, with X-ray absorbing materials, such as barium sulfate or iodinated contrast media, either in whole or in part.

Figure 3:
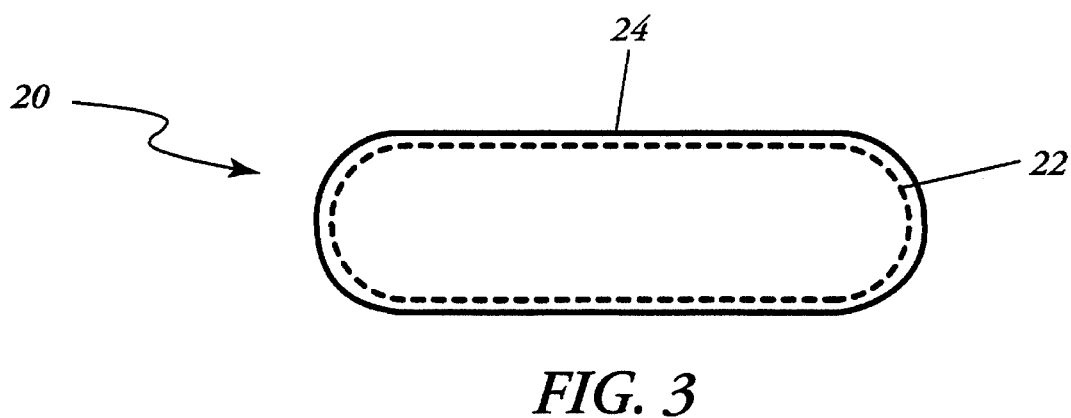
FIG. 3 is a side view of a detectable object marked using a radiopaque coating of the present invention.

Referring now to FIG. 3 there is shown generally at 20 the detectable pellet of the present invention. Pellet 20 has coating 24 and detectable material 22 which is, in the preferred embodiment, barium sulfate. Coating 24 is used to contain detectable material 22 as well as to provide a separation area between multiple detectable pellets 20 which are resident in a user's stomach to enable the attending physician to more easily count the number of detectable pellets 20 in a user's stomach.

Although barium sulfate is used in the preferred embodiment, any inert material which does not react with the individual's digestive track and which shows up under a fluoroscope or absorbs X-rays, can be used. Like any undigested material in an individual's stomach, detectable pellet 20 will eventually pass through the user's bowels. A time release capsule (spherule) would disperse at a predetermined time (e.g., 24 hours) after ingestion. Although pellet 20 shows a coating 24, it will be appreciated that such an overcoat is optional and that a barium sulfate pellet can be fabricated without such a coating if desired. Furthermore, pellet 20 can be a "dummy pill", a quantity of which can be added to a bottle of regular pills. These dummy pills will facilitate subsequent detection, by the use of fluoroscopy or X-rays, of ingested material taken from this particular bottle.

Figure 4:
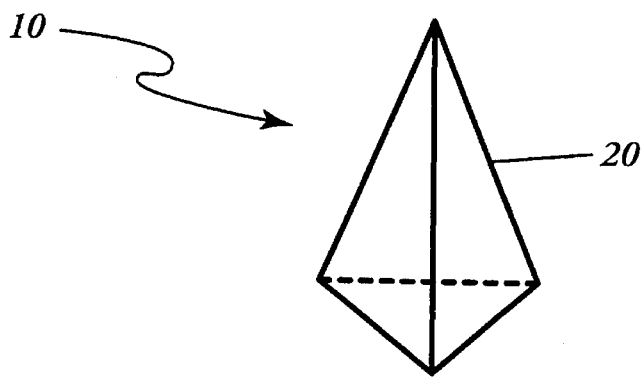
FIG. 4 is a perspective view of a radiopaque marker shaped like a pyramid.

Referring now to FIG. 4 there is shown generally at 10 another embodiment of the device for determining the quantity of a substance ingested by a user. In this instance, object 20 is comprised in whole, or in part, of a radiopaque substance such as barium sulfate. Object 20 can be made in to a solid geometric shape such as a pyramid. Although a pyramid is illustrated in FIG. 4, other shapes are also possible.

Figure 5A:
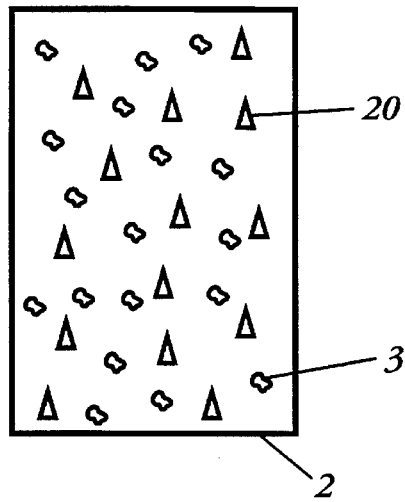
FIG. 5A and FIG. 5B are views of two different boxes of poison, each of which is marked with a radiopaque marker of a different shape.
Figure 5B:
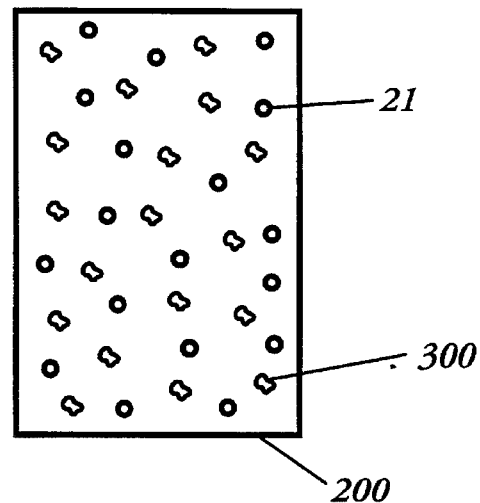

Referring now to FIGS. 5A and 5B there is shown an example application of the shaped, radiopaque markers such as those described in FIG. 4. In this application, container 2 is a box of rat poison pellets 3 and, in contrast, container 200 is a box of ant killer powder 300. After purchase of these two poisonous substances, a parent or caregiver dumps a quantity of pyramid-shaped, radiopaque markers 20 in to the container 2 housing the rat poison. Similarly, a quantity of sphere-shaped, radiopaque markers 21 are added to the ant killer powder 300 in container 200. Now, if a child or unsuspecting individual ingests material from one of these containers, the attending physician can identity the substance ingested. This is done by correlating the shape of the marker image seen on the X-ray with the poisonous substance to which this marker shape was added.

Figure 6:
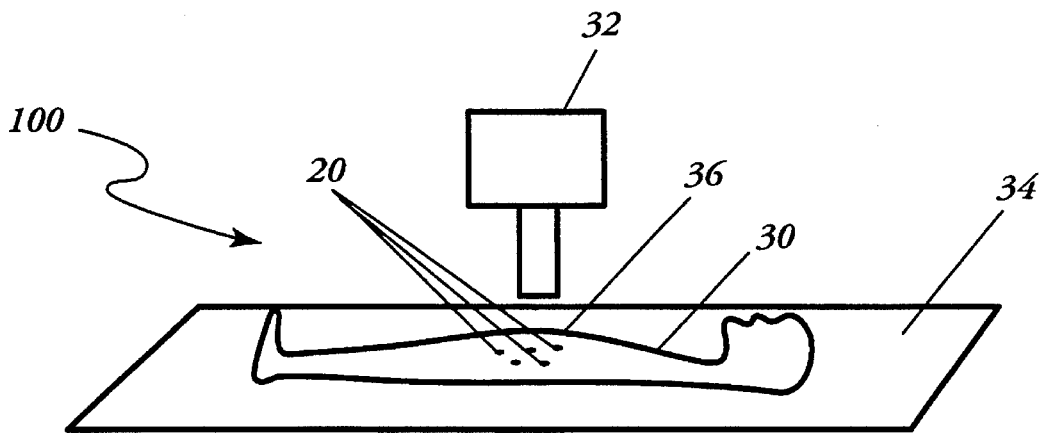
FIG. 6 is a perspective view of the device for determining the number or identity of objects taken by a user showing a fluoroscope, or an X-ray machine, looking into an individual's stomach.

Referring now to FIG. 6 there is shown generally at 100 the system for determining the number of objects taken by a user of the present invention. In this instance, patient 30 lies on X-ray table 34. Fluoroscope or X-ray tube 32 is positioned over the patient's stomach 36. The attending physician can then count the number of detectable pellets 20 which are resident in the patient's digestive track through fluoroscopy or on X-ray film. In the preferred embodiment, pellet 20 is in the shape of a sphere, or other shape which can be conveniently and unambiguously detected on an X-ray. In the preferred embodiment, spherical pellet 20 has a diameter of substantially 0.5 to 1.0 mm (0.7 mm appears to be optimum). If desired, detectable pellet 20 may be affixed to housing 16 using, for instance, a pectin gel for an adhesive. In the preferred embodiment, detectable pellet 20 weighs substantially 1–8 milligrams (3 mg appears to be optimum).

It will be appreciated that the detectable pellet 20 can be incorporated with the foreign substance 12 in a variety of arrangements. If the object 12 is a capsule, the detectable pellet can be attached to the capsule via an adhesive, or by dipping, spraying, dusting or other means. Alternatively, the detectable pellet can be deposited within the bottle of capsules. The tablet or pill can be any type of foreign material subject to being quantified, or identified, with a detectable pellet which is associated with a quantity and type of foreign material. Similarly, if the object 12 is a quantity of material in liquid form, the present system can be used by suspending an iodinated contrast media homogeneously within the liquid. Alternatively, if the object 12 is a quantity of material in powder form, the present system can be used by mixing barium sulfate homogeneously within the powder. The fluoroscope used by the physician to determine the quantity of liquid material in the user's body would then measure the quantity of the iodinated contrast media to assist in determining the quantity of the liquid material taken by the user for purposes of evaluating the appropriate antidote or treatment. Finally, the detectable pellet may be treated or coated with a time release agent which will cause the pellet to maintain its integrity and not be immediately dissolved by the action of stomach enzymes. Thus, the detectable pellet will remain identifiable for a longer period of time in the event the user is not reached for treatment promptly after ingesting the substance, the quantity or identity of which needs to be determined.

The pellets of the present invention should be of unique shapes which are discernable from any angle, such a sphere, pyramid or the like. Multiple pellets of the same or different shapes can be incorporated into a single marker and the relative size, spacing or radiodensity of the pellets within a marker can be used to define the substance with which the markers have been mixed and, also, the strength of the substance. Thus, when two spheres are combined into one marker with one sphere being twice the diameter of the other, that marker would be readily distinguishable. If that marker were mixed with rat poison and a record of that mixture were maintained by the person on whose premises the poison were being stored, if someone ingested a quantity of the poison, the marker could be identified by X-ray and proper treatment immediately prescribed.

Although there have, been described particular embodiments of the present invention of a new and useful device for detecting the number of objects in a user's stomach, it is not intended that such reference, s be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. A method of storage of a toxic substance to facilitate determining information about said substance in the body of a human or an animal after same has been ingested, said method comprising:

a. forming a plurality of distinctive markers from a material detectable by X-ray examination;

b. mixing said markers with a quantity of said substance after the transfer of said substance to a consumer prior to storage of said substance; and c. recording the distinctive features of said markers whereby information about the said substance can be determined by examining said body with an X-ray detection system and comparing the features of the markers shown by the X-ray detection system with the known distinctive features of said markers.

2. A radiographic marker device adapted for attachment to a pill which is to be orally ingested, said device being manufactured, packaged for distribution and distributed separately and independently from the pill to which it is adapted to be attached so that it can be attached to the pill after the pill is in the possession of a consumer, said device comprising:

a. a pill coating formable into a shape to conform said coating to the exterior contours of said pill;

b. a radio-opaque substance integral to said pill coating; and c. means integral to said coating to secure said coating about the contours of said pill.

3. The device of claim 2 wherein said radio-opaque substance is formed into a predetermined, distinct shape.

4. An article to facilitate the determination of features of the substance of a pill after the pill has been ingested by an animal without resorting to intrusive procedure, said article consisting of a marker of a predetermined, defined shape, said marker made from a material detectable by an X-ray examination system, and means for attaching said marker to said pill.

5. An article to facilitate the determination of features of the substance of a pill after the pill has been ingested by an animal without resorting to intrusive procedure, said article manufactured, packaged for sale, and sold independently of and separate from the pill, said article comprising a marker of a predetermined defined shape, said marker made from a material detectable by an X-ray examination system, and means for attaching said marker to said pill, wherein said means for attaching said marker to said pill includes forming the said marker into a cover shaped to mate with a portion of the outside shape of said pill and of a complimentary size whereby said marker can be attached to the pill after the pill is in the possession of a consumer, said attachment being via a friction fit between the inside of said cover and the outside of said pill when the cover is placed about said pill.

6. An article to facilitate the determination of features of the substance of a pill after the pill has been ingested by an animal without resorting to intrusive procedure, said article comprising a marker of a predetermined defined shape, said marker made from a material detectable by an X-ray examination system, and means for attaching said marker to said pill, wherein said marker is formed from two or more pellets with one pellet having a defined size relative to the remaining pellet(s).

7. An article to facilitate the determination of features of the substance of a pill after the pill has been ingested by an animal without resorting to intrusive procedure, said article comprising a marker of a predetermined defined shape, said marker made from a material detectable by an X-ray examination system, and means for attaching said marker to said pill, wherein said marker is formed from two or more pellets with one pellet spaced a defined distance from the remaining pellet(s).

8. An article to facilitate the determination of features of the substance of a pill after the pill has been ingested by an animal without resorting to intrusive procedure, said article comprising a marker of a predetermined defined shape, said marker made from a material detectable by an X-ray examination system, and means for attaching said marker to said pill, wherein said marker is formed from two or more pellets with one pellet having a defined radiodensity relative to the remaining pellet(s).

9. A method of handling of pharmaceutical products after the said pharmaceutical products have been manufactured and distributed to consumers by the manufacturer thereof and are in the possession of a consumer, said product being distributed in the form of a pill, capsule or tablet, said method intended to facilitate determining information about said product in the body of a human or an animal after same has been ingested, said method comprising:

a. forming a plurality of distinctive markers from a material detectable by X-ray examination;

b. providing said markers with means for attaching them to said products; and c. packaging and distributing said markers independently of said products whereby the consumer can acquire said markers independently of said products for attachment to said products after gaining possession of said products from the manufacturer thereof to enable said product to be identified after the product has been ingested in the body of an animal by examining said body with an X-ray detection system to determine the distinctive features of the marker attached to said product and comparing the features of the markers shown by the X-ray detection system with the known distinctive features of said markers.

* * * * *